US00PP37221P2

(12) United States Plant Patent
von Tubeuf

(10) Patent No.: US PP37,221 P2
(45) Date of Patent: Jan. 20, 2026

(54) POINSETTIA PLANT NAMED 'NPCW24408'

(50) Latin Name: *Euphorbia pulcherrima*
Varietal Denomination: NPCW24408

(71) Applicant: KLEMM + SOHN GMBH & CO. KG, Stuttgart (DE)

(72) Inventor: Guido von Tubeuf, Stuttgart (DE)

(73) Assignee: Klemm + Sohn Gmbh & Co. KG, Stuttgart (DE)

( * ) Notice: Subject to any disclaimer, the term of this patent is extended or adjusted under 35 U.S.C. 154(b) by 0 days.

(21) Appl. No.: 19/010,890

(22) Filed: Jan. 6, 2025

(51) Int. Cl.
*A01H 5/02* (2018.01)

(52) U.S. Cl.
USPC ..... Plt./307

(58) Field of Classification Search
USPC ..... Plt./307
CPC ... A01H 5/12; A01H 5/02; A01H 5/00; A01H 6/385; A01H 6/38
See application file for complete search history.

(56) References Cited

PUBLICATIONS

Fleuro Select IPM Essen 2024, retrieved on Mar. 19, 2025 at https://www.fleuroselect.com/events/show/ipm-essen-2024, one page. (Year: 2024).*

Floral Daily, Selecta to showcase colorful varieties at IPM 2024, retrieved on Mar. 19, 2025 at https://www.floraldaily.com/article/9584137/selecta-to-showcase-colorful-varieties-at-ipm-2024/, 2023, 5 pp. (Year: 2023).*

Selecta One Home Poinsettia, Kalanchoe & Campanula 2024, retrieved on Mar. 19, 2025 at https://www.gradinaspa.com/part/katalog-selecta-poinsettia-kalanchoa-i-campanula-2024.pdf, 2 introductory pages, pp. 8-9. (Year: 2024).*

* cited by examiner

*Primary Examiner* — June Hwu
(74) *Attorney, Agent, or Firm* — Weatherly IP Solutions, LLC; Karen P. Bechtold; James Weatherly

(57) ABSTRACT

A new poinsettia plant particularly distinguished by rich, dark, deep red-colored bracts, is disclosed.

1 Drawing Sheet

Genus and species: *Euphorbia pulcherrima.*
Variety denomination: 'NPCW24408'.

BACKGROUND OF THE NEW PLANT

The present invention comprises a new and distinct variety of poinsettia, botanically known as *Euphorbia pulcherrima* and hereinafter referred to by the variety name 'NPCW24408'. 'NPCW24408' was identified in Nairobi, Kenya in December 2018 as a cross-pollination from female parent EP-2015-5025 (unpatented) and male parent NPCW19282 (U.S. Plant Pat. No. 32,726). A seedling was selected in October 2019 and named 'NPCW24408'.

In May 2020, 'NPCW24408' was first vegetatively propagated by apical cuttings in Stuttgart, Germany and was found to reproduce true to type in successive generations of asexual propagation via apical cuttings.

SUMMARY

The following are the most outstanding and distinguishing characteristics of this new variety when grown under normal horticultural practices in Stuttgart, Germany.

1. Rich dark red colored bracts.

DESCRIPTION OF THE PHOTOGRAPH

This new poinsettia plant is illustrated by the accompanying photograph which shows an overall view of the plant. The photograph is of a plant approximately fourteen-weeks-old, grown indoors in Stuttgart, Germany in December 2022. The colors shown are as true as can be reasonably obtained by conventional photographic procedures.

DESCRIPTION OF THE NEW VARIETY

The following detailed descriptions set forth the distinctive characteristics of 'NPCW24408'. The data which define these characteristics were collected from asexual reproductions carried out in Stuttgart, Germany. Data was collected on eighteen-week-old plants grown indoors in Stuttgart, Germany under greenhouse conditions in November 2024. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW24408'.

Parentage:
- *Female.*—Poinsettia variety EP-2015-5025 (unpatented).
- *Male.*—Poinsettia variety 'NPCW19282' (U.S. Plant Pat. No. 32,726).

Plant:
- *Form.*—Triangular.
- *Growth habit.*—Upright.
- *Height.*—37.0 cm to 39.0 cm.
- *Width.*—35.0 cm to 40.0 cm.
- *Average number of inflorescences per plant.*—5.

*Keeping quality*.—Very good (4 out of 5 based on a scale of 0 to 5 shelf-life test).
*Time to produce a cutting*.—5 weeks.
*Flowering response time*.—Approximately 56 days.
*Propagation type*.—Apical cuttings.
*Rooting habit and root color*.—Freely branching and white (RHS NN155C).

Lateral branches:
*Color*.—RHS 143A.
*Length*.—22.0 cm to 26.0 cm.
*Internode length*.—2.0 cm to 4.0 cm.
*Diameter*.—0.5 to 0.8 cm.
*Branching habit*.—Freely branching.
*Number of lateral branches per plant*.—5 to 6.
*Texture*.—Smooth.
*Strength*.—Strong.

Leaves:
*Quantity*.—5 to 6 per lateral branch.
*Arrangement*.—Alternate.
*Number of lobes on the leaf blade*.—0 to 2.
*Lobation depth*.—Shallow.
*Depth of the deepest sinus of the leaf blade*.—0.5 cm.
*Shape*.—Ovate.
*Apex*.—Acute.
*Base*.—Obtuse.
*Margin*.—Entire.
*Length*.—10.0 cm to 13.0 cm.
*Width*.—7.0 cm to 9.0 cm.
*Texture (both upper and lower surfaces)*.—Upper: Smooth. Lower: Slightly pubescent.
*Vein color*.—Upper surface: Transparent. Lower surface: RHS 139D.
*Variegation*.—Absent.
*Venation pattern*.—Reticulate.
*Color*.—Mature foliage: Upper surface: RHS 139A. Lower surface: RHS 137B. Immature foliage: Upper surface: RHS 141A. Lower surface: RHS 139B.
*Leaf petiole*.—Length: 3.5 cm to 5.0 cm. Diameter: 0.2 cm to 0.3 cm. Color: Upper (part) surface: RHS 59A. Lower (part) surface: RHS 181A. Texture: Smooth. Strength: Strong.
*Transitional leaves*.—Amount: Sparse. Shape: Ovate. Length: 8.0 cm to 10.0 cm. Lobing: Weak. Width: 5.0 cm to 6.0 cm. Color: Upper surface: RHS 203C and RHS 46A, both colors spread throughout the leaf surface with more concentration of RHS 46A toward the bract margins. Lower surface: RHS 137B and RHS 46A, both colors spread throughout the leaf surface with more concentration of RHS 46A toward the bract margins.

Inflorescence:
*Type and habit*.—Cluster of cyathia.
*Quantity per lateral branch*.—1.
*Position relative to foliar plane*.—Above.
*Lastingness of inflorescence on the plant*.—6 to 8 weeks.
*Natural flowering season*.—November and December.
*Diameter*.—20.0 cm to 23.0 cm.
*Height*.—3.0 cm to 4.0 cm.
*Fragrance*.—Absent.

Bracts:
*Number of bracts per inflorescence*.—6 to 7.
*Shape*.—Ovate.
*Apex*.—Acute.
*Base*.—Obtuse.
*Margin*.—Entire.
*Size*.—Length: 7.0 cm to 11.0 cm. Width: 4.5 cm to 7.0 cm.
*Texture (both upper and lower surfaces)*.—Smooth.
*Folding along the main vein*.—Absent.
*Twisting*.—Absent.
*Rugosity between the veins*.—Medium.
*Venation pattern*.—Reticulate.
*Vein color*.—Upper surface: RHS 59A. Lower surface: RHS 181A.
*Bract color*.—Upper surface: RHS 46A. Lower surface: RHS 47A.
*Bract petiole*.—Length: 0.5 cm to 2.5 cm. Diameter: 0.2 cm to 0.3 cm. Color: Upper (part) surface: RHS 59A. Lower (part) surface: RHS 181A. Texture: Smooth. Strength: Sturdy.

Cyme:
*Diameter*.—1.0 cm to 2.0 cm.
*Cyathia number*.—4 to 6 per inflorescence.
*Deformation of glands of the cyathium*.—Absent.
*Timing of opening of cyathia*.—Beginning of December, first pollen appears in parallel to opening of the nectar cups, stigmas appear 2 weeks later.
*Cyathium*.—Shape: Ovate. Texture (inner and outer surfaces): Smooth. Diameter: 0.2 cm to 0.5 cm. Length: 0.3 cm to 0.6 cm. Color: RHS 143B.
*Peduncle*.—Color: RHS 142B. Length: 0.2 cm. Diameter: 0.1 cm. Texture: Smooth. Strength: Medium.
*Nectar cups*.—Number: 1 per cyathium. Diameter: 0.1 cm. Length: 0.4 to 0.5 cm. Color: RHS 13B. Shape: Lip shaped. Texture (both inner and outer surfaces): Smooth.

Reproductive organs:
*Stamen quantity*.—10 to 12 per cyathium.
*Stamen shape*.—Ovate.
*Filament length*.—0.3 cm.
*Filament color*.—RHS 39A.
*Pollen quantity*.—Moderate.
*Pollen color*.—RHS 6A.
*Gynoecium*.—Present. Pistil quantity per cyathium: 1. Pistil length: 0.2 cm. Stigma form: Divided in 2 parts. Stigma color: RHS 183A. Style length: 0.2 cm. Style color: RHS 183A. Ovary length: 0.05 cm. Ovary color: RHS 143C.

Fruit and seed set: None observed.

Disease and insect resistance: No particular disease or insect resistance observed.

COMPARISON WITH PARENTAL LINE AND KNOWN VARIETY

'NPCW24408' is distinguished from its parents as described in Table 1:

TABLE 1

Comparison with Parental Lines

| Trait or characteristic | 'NPCW24408' | Female parent 'EP-2025-5025' | Male Parent 'NPCW19282' |
|---|---|---|---|
| Bract color | Rich dark red | Pale red | Rich medium to dark red but lighter than 'NPCW24408 |

TABLE 1-continued

| Comparison with Parental Lines | | | |
|---|---|---|---|
| Trait or characteristic | 'NPCW24408' | Female parent 'EP-2025-5025' | Male Parent 'NPCW19282' |
| Bract shape | Medium elongated | Elongated | More rounded |
| Leaf size | Medium to large | Large | Small to medium |

COMPARISON WITH SIMILAR VARIETY

'NPCW24408' is most similar to the commercial poinsettia plant named Grande Italia (patent status unknown). Differences between the two varieties are described in Table 2:

TABLE 2

| Trait or characteristic | 'NPCW24408' | Commercial line: Grande Italia |
|---|---|---|
| Rugosity between veins | Moderate | Shallow |
| Bract colour quality | Richer, deeper red color than Grande Italia | Duller red color than 'NPCW24408' |
| Bract orientation | More upright than Grande Italia | More horizontal than 'NPCW24408' |

I claim:

1. A new and distinct cultivar of Poinsettia Plant Named 'NPCW24408' as shown and described herein.

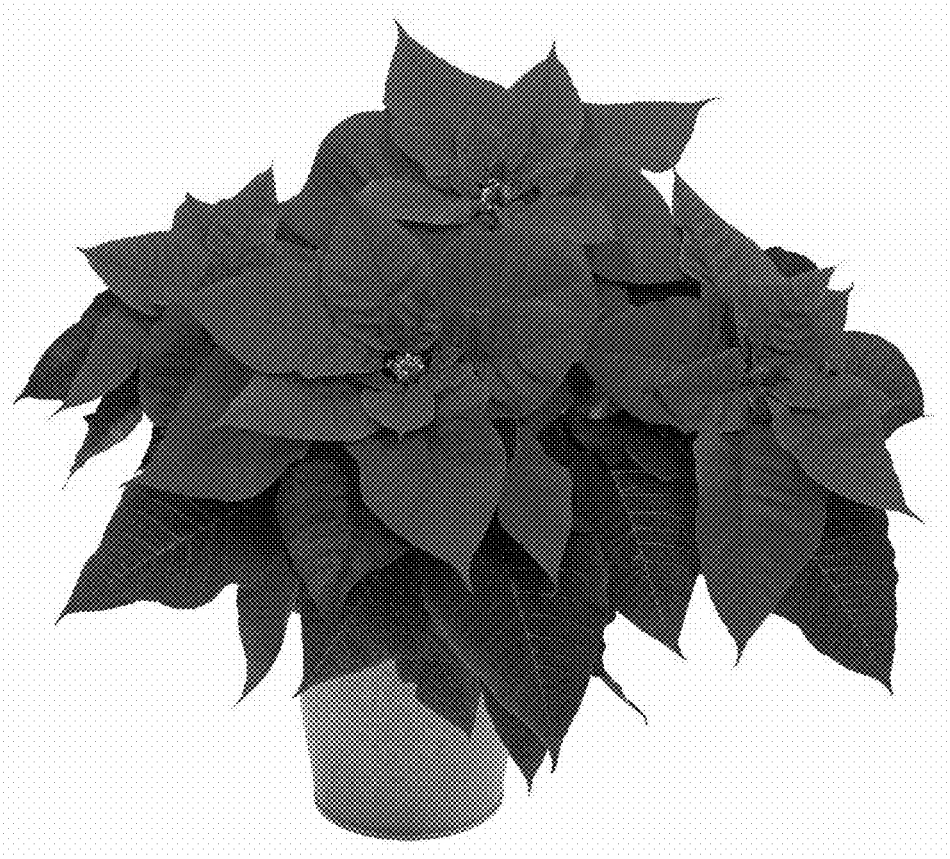

* * * * *